United States Patent [19]  
Prodosmo et al.

[11] Patent Number: 4,777,832  
[45] Date of Patent: Oct. 18, 1988

[54] LIQUID LEVEL SENSOR, USED IN AN AUTOMATIC STATION FOR PREPARING IMMUNOLOGIC DOSAGES

[75] Inventors: Armando Prodosmo; Federico Mazzacurati, both of Rome, Italy

[73] Assignee: Chemila S R L, Italy

[21] Appl. No.: 930,642

[22] Filed: Nov. 14, 1986

[30] Foreign Application Priority Data

Nov. 18, 1985 [IT] Italy ................... 48804 A/85

[51] Int. Cl.$^4$ ............... G01N 35/00; G01F 23/24
[52] U.S. Cl. ........................... 73/863.02; 222/64; 23/304 R; 23/864.16
[58] Field of Search ......... 73/863.02, 304 R, 864.11, 73/864.15, 864.16, 864.22; 222/364, 64

[56] References Cited

U.S. PATENT DOCUMENTS

| 2,423,397 | 2/1947 | Loumiet et al. | 73/304 R |
| 3,477,460 | 11/1969 | Dotto | 73/304 R X |
| 3,687,289 | 8/1972 | Tischler | 73/863.02 X |
| 3,813,945 | 6/1974 | Crumel | 73/863.02 |

FOREIGN PATENT DOCUMENTS

| 1342284 | 9/1963 | France | 73/304 R |
| 844010 | 8/1960 | United Kingdom | 73/304 R |

Primary Examiner—Tom Noland  
Attorney, Agent, or Firm—Ostrolenk, Faber, Gerb & Soffen

[57] ABSTRACT

A new liquid level sensor, suitable for use as an auxiliary device in an automatic station for preparing immunologic dosages, consists of a U pipe containing water, and provided with a resistivity sensor at the end of one of its branches, the other branch being connected with the terminal of the liquid dispensing or suction system of the automatic station in such a way that a very small pressure difference within the system results in a water level variation in both branches and in the relevant activation (or disactivation) of the resistivity sensor.

20 Claims, 5 Drawing Sheets

LIQUID LEVEL SENSOR, USED IN AN AUTOMATIC STATION FOR PREPARING IMMUNOLOGIC DOSAGES

BACKGROUND AND SUMMARY OF THE INVENTION

The present invention relates to auxiliary devices for automatic equipment, particularly liquid level sensors.

More particularly, the invention relates to a liquid level sensor suitable as an auxiliary device in an automatic station for preparing immunologic dosages.

The determination for diagnostic purposes of substances present in the blood at very low concentrations, such as hormones, drugs, proteins etc., is possible nowadays by the use of immunologic dosage technologies (RIA, EIA, etc.,) characterised by a very high sensitivity.

The preparation of such dosages which require incubation, in a single test-tube, of several substances (e.g. unknown antigen, marked antigen, specific antibody), is carried out in several phases.

One phase is the suction, from several containers or test tubes, of liquids containing the reagents, and subsequently the dispensing of these liquids into the test tubes where the reactions are to take place.

These operations are generally performed manually by an operator using dispensing pipettes.

In recent years, within the scope of the automation process regarding all the phases of immunologic dosage preparation, computerized stations for the dispensing of dosage liquids have been developed.

A typical automatic station consists of a computer controlling the operation of:
 a plotter for positioning X, Y, Z of a dispensing probe on an operation surface carrying the dosage trays;
 a diluter, connected to the probe, for suctioning and dispensing the liquids.

The diluter is normally made up by one or more syringes, connected by means of flexible tubes, to the probe of the plotter.

The suction and dispensing operations are carried out by moving the syringe piston up or down.

The plotter probe is called usually z-axis, and has no fixed needle, but uses tips which, at intervals, are taken from a suitable tray and automatically changed after each dispensing operation, so as to avoid any possible contamination. Usually, during operation of the preparing station, the tip collects several times from the same test tube (or container) well determined quantities of the liquid to be dispensed.

Therefore, taking into account that the liquid quantity in the test tube decreases according to the number of withdrawals, it is necessary that the system should know, before each suction, the quantity of liquid available as compared with the required quantity. That is, it is necessary to know, before withdrawing, the volume of liquid contained in the test tube. However, since the geometry of the liquid is known, it is sufficient to know one parameter only: the liquid level in the test tube. To obtain this information, it has been necessary to create a system which, during the lowering of the z-axis into the test tube, is able to:
 rapidly block the movement as soon as the tip of the z-axis touches the free surface of the liquid,
 signal to the computer the level reached by the tip, in respect to a reference quota (z-home).

This system permits the computer to know the level, and therefore the volume, of the liquid contained in the test tube. If the quantity of liquid is sufficient to satisfy the request, the computer can at this point lower the tip with reference to the free surface of the liquid, to a depth corresponding to the volume of liquid to be withdrawn, thus avoiding lowering the tip more than necessary.

The operation could be even more refined by performing in subsequent steps, small immersions of the tip with alternate suctioning of small volumes of liquid until the total volume to be withdrawn has been reached; in this manner only a small portion of the tip is maintained immersed in the liquid. The sensors more commonly used to detect liquid levels are the capacity and resistivity types. Capacity sensors detect the difference in the dielectric constant, and therefore the capacity, when there are variations in the media in which they are immersed. The resistivity sensors make use of the conductivity of the liquid in which they are immersed, which short-circuits the two electric contacts.

Unfortunately the direct application of these sensors for the system in question would be impossible, at least for the following reasons:

(1) The different liquids to be suctioned, in order to prepare the dosages, have electric properties which differ between them; for instance, not all the liquids have good conductivity. Therefore, there is low reliability of the signals given by the sensors.

(2) The sensor should be fastened to the tip of the z-axis which, as already mentioned, is not always the same, but is automatically replaced after each dispensing operation. Therefore it would be impractical and very expensive to have all tips with the sensors incorporated.

Even one of the commonly used pressure sensors, for instance a piezometric resistivity pressure transducer, would not be directly applicable in this system. In fact, the use of such device in the dispensing system, as shown in FIGS. 1 and 2, cannot give satisfactory results due to the scarce sensitivity of the pressure sensors available on the market.

It has now been found that the above described problem can be solved by installing a new level sensor consisting of an U pipe containing water and provided with a resistivity sensor at the end of one of its branches, the other branch being connected with the terminal of the liquid suction or dispensing system of the automatic station in such a way that a minimum difference of pressure within the system results in a water level variation in both branches and consequently in the activation (or disactivation) of the resistivity sensor.

BRIEF DESCRIPTION OF THE DRAWINGS

The invention will be better understood by reading the following detailed description, to be considered together with the attached drawings, where a typical automatic station for preparing immunologic dosages includes a computer which controls the operations of a plotter for positioning a dispensing probe on a working surface containing the dosage trays, and a diluter, connected to the probe, for the suction and dispensing of the liquids.

FIG. 1 shows the situation wherein the tip of the z-axis is not in contact with the liquid; in this case the air flows from the orifice of the tip itself and no internal pressure is created.

FIG. 2 shows the situation wherein the tip comes into contact with the liquid free surface in the test tube (or in the container of a reagent), in which case the orifice is immersed and consequently an overpressure is created, which activates the pressure switch. As mentioned above, this solution, even if theoretically valid, cannot give satisfactory results because of the low sensitivity of the existing devices.

DETAILED DESCRIPTION

Figure 1:
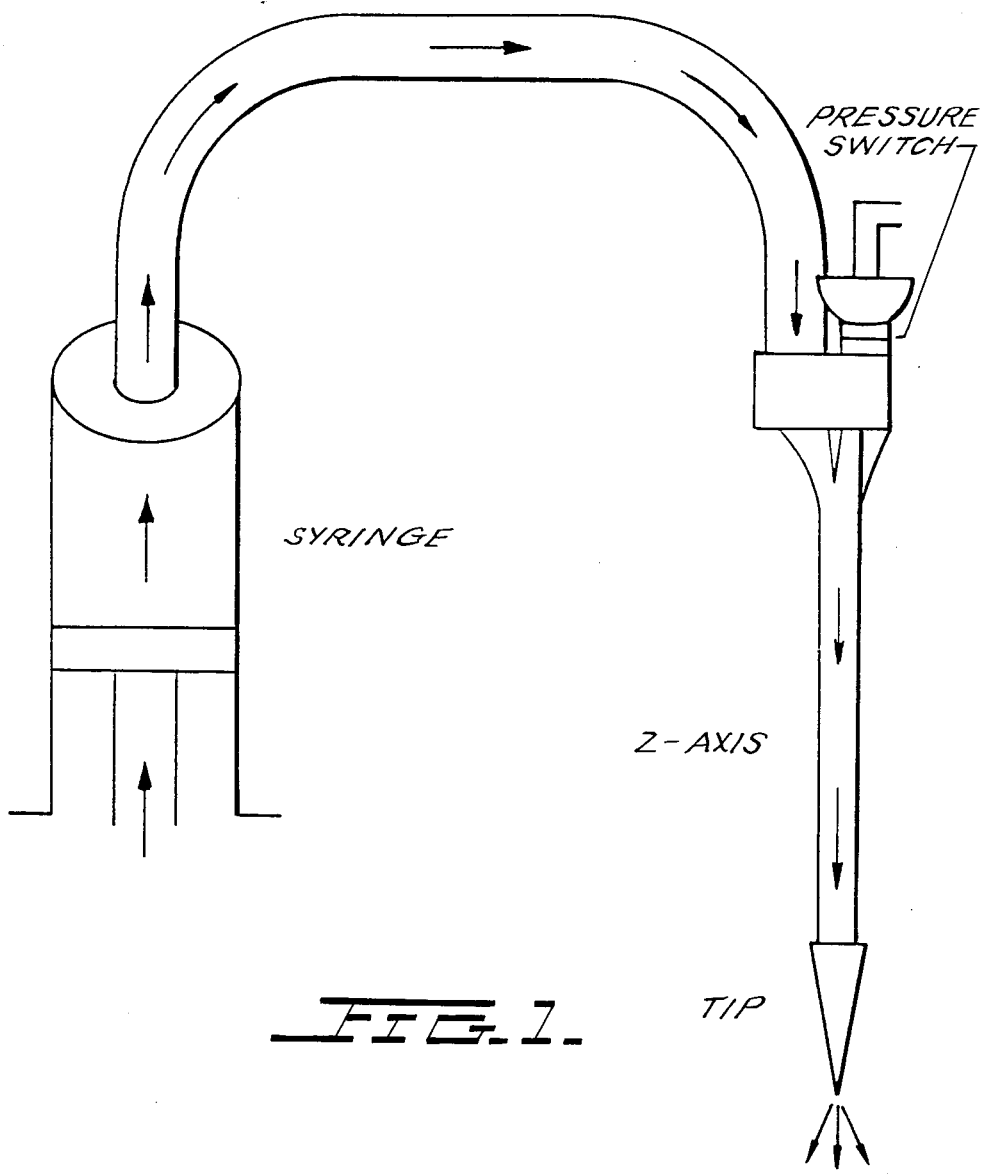
FIGS. 1 and 2 show a theoretical solution of the problem of detecting a liquid level with the necessary degree of sensitivity by using a pressure transducer.
Figure 2:
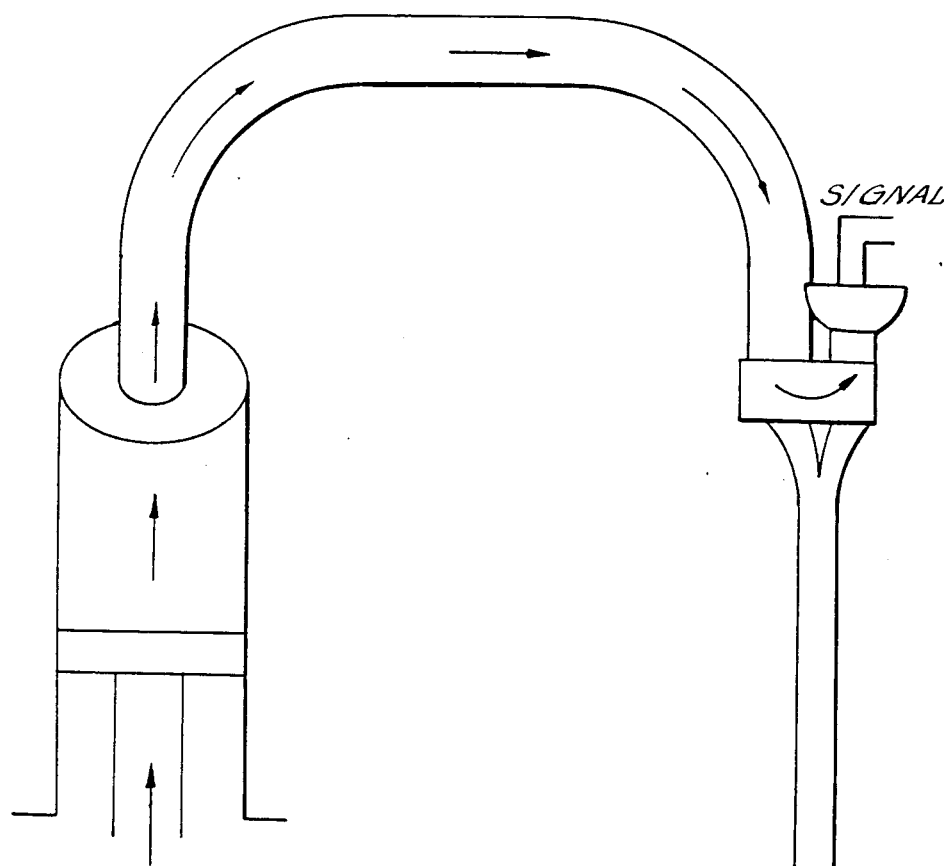
Figure 3:
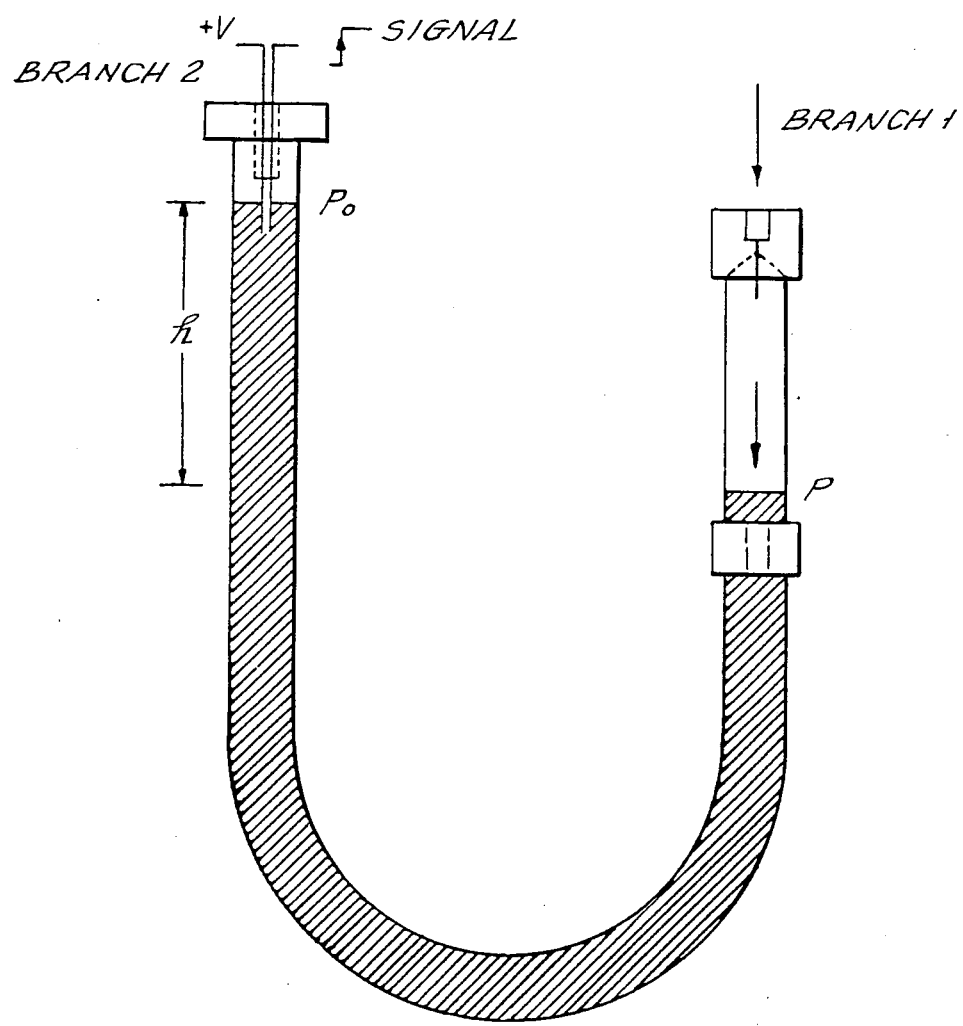
FIGS. 3, 4 and 5 show the device according to the present invention, as such (FIG. 3), when installed in the dispensing system (FIG. 4), and when activated due to the contact of the tip with the liquid free surface (FIG. 5). These figures may be helpful in understanding the detailed description which follows.

The liquid level sensor according to the invention consists of a U pipe containing water (FIG. 3). Both free surfaces of the water, under atmospheric pressure, are generally at the same level, according to the law of communicating containers.

Should the pressure in branch 1 be increased, the water level in this branch is lowered, thus raising the water level in branch 2. Since a resistivity sensor has been installed at the end of branch 2 of the U pipe, should the quantity of water be kept within certain limits, the sensor contacts will be reached by the water due to very low increases in pressure.

If one of the two sensor contacts is connected to a voltage source V, this, due to the water conductivity, will be transferred to the other contact and generate a signal which may be used by the computer.

Figure 4:
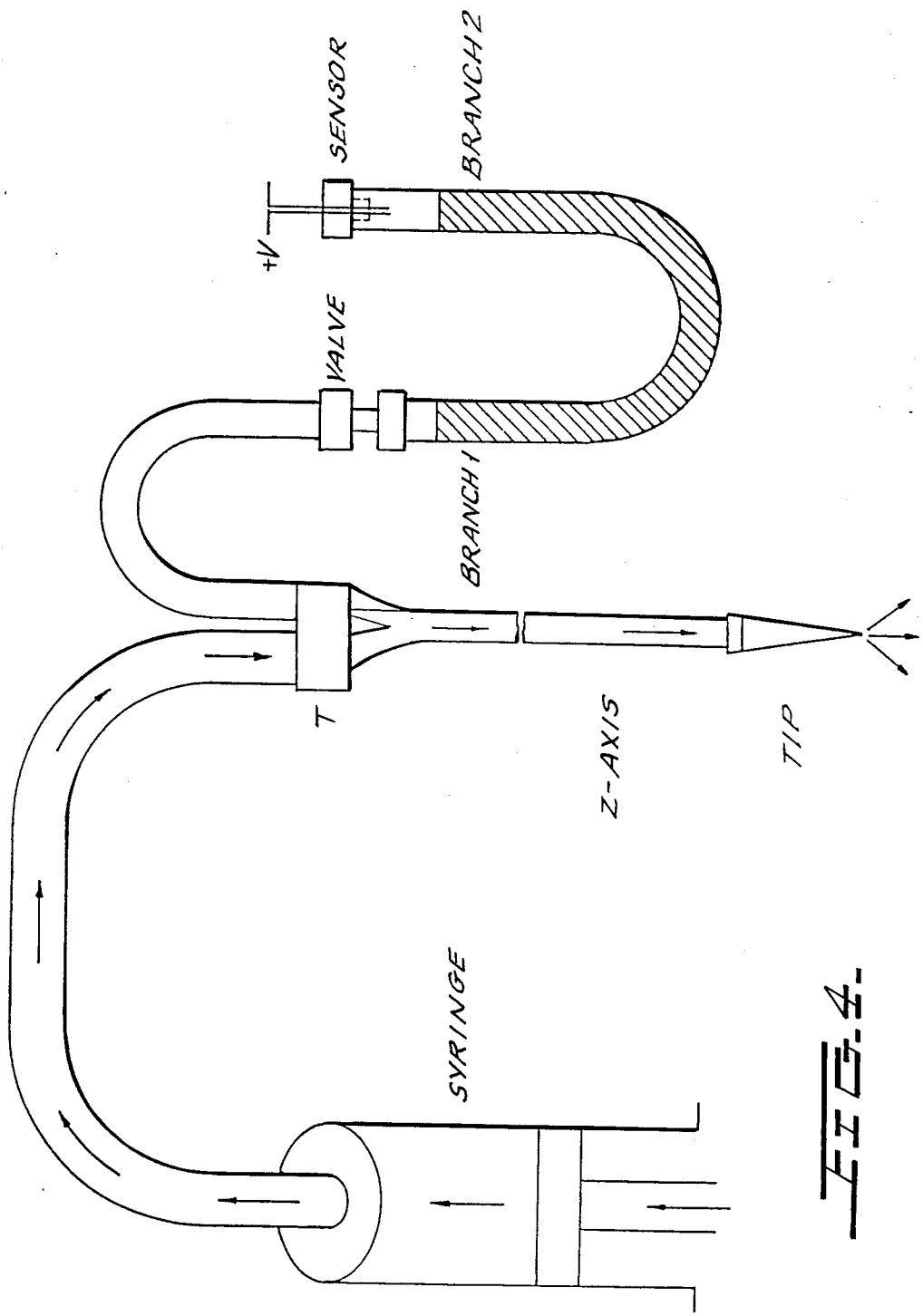

The above described device is used to detect the liquid levels in the test tubes by means of the operating connection shown in FIG. 4. The z-axis of the preparing station is connected, through a suitable T-member:
from one side, to the dilutor syringe;
from the other side, to branch 1 of the U-pipe.
By moving up the syringe piston, a movement of air toward the z-axis is obtained. If the z-axis tip is not in contact with the liquid surface, the air flows through the orifice of the tip itself. Moreover, if the syringe piston comes up slowly, the air flows out easily, without creating any pressure in the internal connections.

Figure 5:
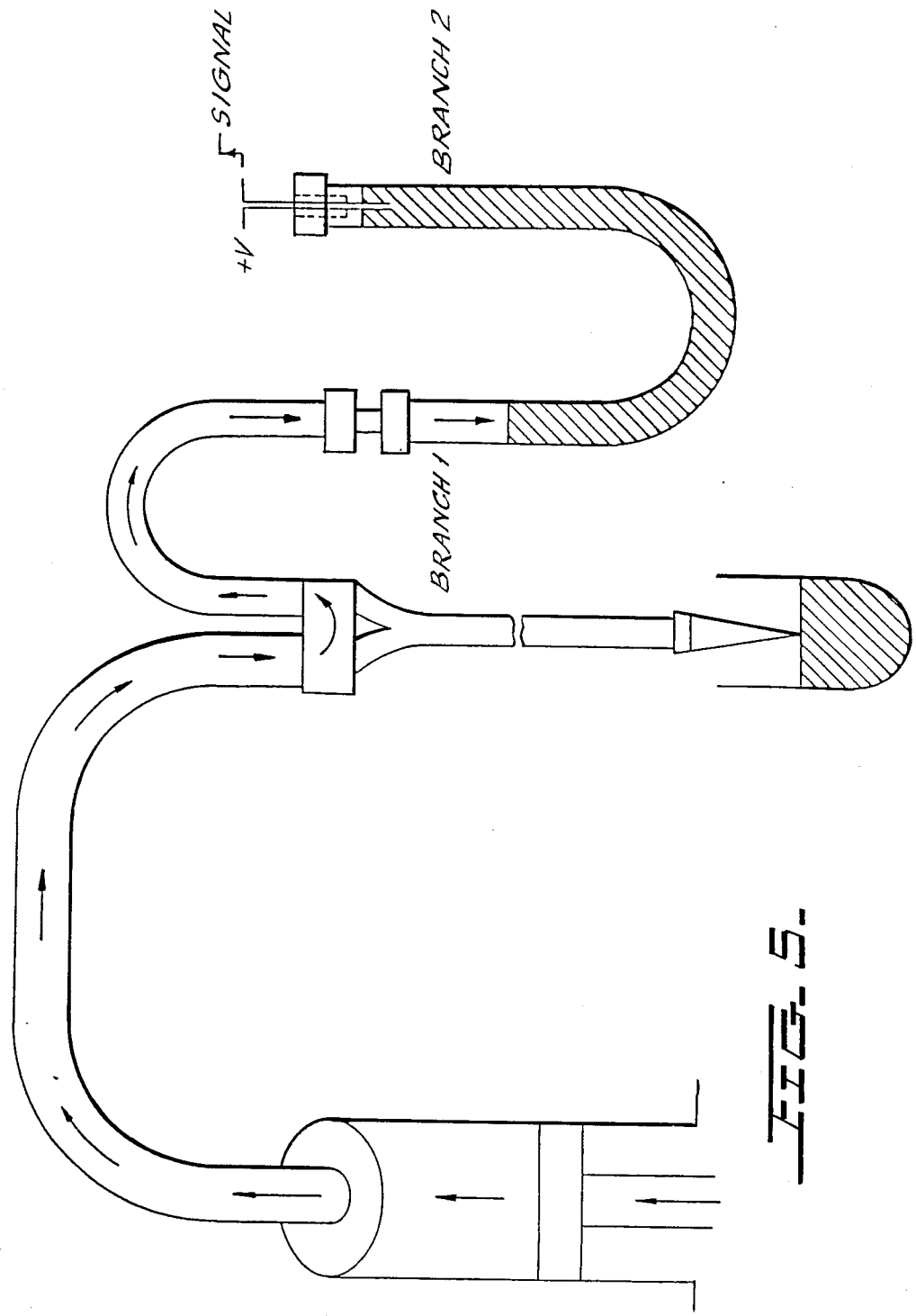

As soon as the tip comes into contact with the liquid free surface of the test tube (or container), the air flow is stopped, thus causing an immediate increase in pressure within the connections. This pressure increase is transmitted to the branch 1 of the U-pipe, causing a quick displacement of the water (FIG. 5). The level increase in branch 2 activates the sensor which transmits the electric signal to the computer.

A preferred form provides for the connection of the operational device according to the invention, to the dispensing system through an electrically controlled valve, place at the input of branch 1. (FIG. 4).

The purpose of the valve is to keep the connection open only during the phase of use of the sensor level. During the other phases, i.e. during suction and dispensing of the liquids, the connection should be interrupted in order to permit a correct execution of these operations. The valve is automatically activated and disactivated by the computer.

It should be obvious for any technician that the invention is not limited to the embodiment form as herein described and illustrated.

For instance, the liquid contained in the U-pipe, exemplified as water, could be any liquid endowed with conductivity suitable for the resistivity sensor used.

Furthermore, the herein described liquid level sensor, which embodies an appropriate sensitivity together with structural simplicity, may be used as an auxiliary means in any system whereby it is necessary to determine the level of a liquid and translate it into an immediate return signal to the control unit. Therefore, its use is not limited to automatic stations for preparing immunologic dosages.

We claim:

1. A liquid level operated sensor suitable for use in connection with an automatic station for suction or dispensing of liquids in containers which comprises a U-shaped container means having first and second legs, a conductive fluid in said container means and incompletely filling said container means, a resistivity sensor capable of providing an output signal disposed in the first leg of said container means, and means to connect the second leg to a pressure operated apparatus such that minimal change in the pressure in said apparatus is communicated to the conductive fluid in said container means and causes the conductive fluid to move into or out of contact with said sensor.

2. The sensor of claim 1 wherein said means to connect comprises a valve means.

3. The sensor of claim 2 wherein said valve means is an electrically controlled valve means.

4. The sensor of claim 1 wherein said sensor is disposed in said first leg at a point which is normally out of contact with said conductive fluid.

5. The sensor of claim 4 wherein said sensor is disposed at the end of said first leg remote from said second leg.

6. The combination, a pressure operated apparatus and the liquid level operated sensor of claim 5.

7. The sensor of claim 1 further comprising means to cause the resistivity sensor to generate an output signal when in contact with said conductive fluid.

8. The sensor of claim 7 further comprising means to control the pressure in said apparatus in response to the output signal of said resistivity sensor operatively connected to said sensor.

9. In combination, a pressure operated apparatus and the liquid level operated sensor of claim 7.

10. In a method of operating an apparatus for liquid removal or dispensing into containers by altering the pressure in the apparatus, the improvement which comprises connecting the liquid level operated sensor of claim 7 to said apparatus and adjusting the pressure within the apparatus in response to the output signal of the resistivity sensor.

11. The method of claim 10 in which the pressure adjustment is in response to the presence of the output signal.

12. The method of claim 10 in which the pressure adjustment is in response to the magnitude of the output signal.

13. The sensor of claim 1 wherein said U-shaped container is a U-shaped tube.

14. The sensor of claim 13 wherein said means to connect is an electrically operated valve and further comprising means to cause the resistivity sensor to generate an output signal when in contact with said conductive fluid and means to control both the pressure in the apparatus and the valve in response to the output signal of the sensor operatively connected to the sensor.

15. In combination, a pressure operated apparatus and the liquid level operated sensor of claim 14.

16. In combination, a pressure operated apparatus and the liquid level operated sensor of claim 1.

17. The combination of claim 16 wherein said pressure operated apparatus comprises a pressure operated pipet.

18. In a method of operating an apparatus for liquid removal or dispensing into containers by altering the pressure in the apparatus, the improvement which comprises connecting the liquid level operated sensor of claim 1 to said apparatus and adjusting the pressure within the apparatus in response to the output signal of the resistivity sensor.

19. The method of claim 18 in which the pressure adjustment is in response to the presence of the output signal.

20. The method of claim 18 in which the pressure adjustment is in response to the magnitude of the output signal.

* * * * *